(12) United States Patent
Ohsawa et al.

(10) Patent No.: US 7,037,934 B2
(45) Date of Patent: May 2, 2006

(54) BLOOD LIPID AMELIORANT COMPOSITION

(75) Inventors: Tsuneki Ohsawa, Tokyo (JP); Ikuo Takagi, Matsudo (JP); Ippei Shimizu, Tokyo (JP); Tatsuhito Kondo, Tokyo (JP); Masato Nakayama, Saitama (JP); Yasuhiro Torizumi, Ryugasaki (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/460,535

(22) Filed: Jun. 11, 2003

(65) Prior Publication Data

US 2004/0023919 A1 Feb. 5, 2004

Related U.S. Application Data

(63) Continuation-in-part of application No. PCT/JP01/10913, filed on Dec. 12, 2001.

(30) Foreign Application Priority Data

| Dec. 14, 2000 | (JP) | 2000-379880 |
| Dec. 13, 2001 | (JP) | 2001-380094 |
| Dec. 13, 2001 | (TW) | 90130882 A |

(51) Int. Cl.
*A61K 31/40* (2006.01)
*A61K 31/355* (2006.01)
*A61K 31/375* (2006.01)
*A61K 31/525* (2006.01)
*A61K 31/185* (2006.01)

(52) U.S. Cl. ............... 514/423; 514/251; 514/458; 514/474; 514/553; 514/616

(58) Field of Classification Search ........... 514/251, 514/427, 458, 474, 616, 665, 553, 423
See application file for complete search history.

(56) References Cited

U.S. PATENT DOCUMENTS 5,662,934 A 9/1997 Najarian

FOREIGN PATENT DOCUMENTS

| EP | 933080 A | 8/1999 |
| JP | 55-76816 A | 6/1980 |
| JP | 58-69813 A | 4/1983 |
| JP | 60-41611 A | 3/1985 |
| WO | WO 94/15592 A1 | 7/1994 |
| WO | WO 97/38694 A1 | 10/1997 |

OTHER PUBLICATIONS

Faggiotto et al., Current Opinion in Lipidology (1998) 9/6 (541-549) (abstract).*
Aviram, et al., "Atorvastatin and gemfibrozil metabolites, but not the parent drugs, are potent antioxidants against lipoprotein oxidation", *Atherosclerosis*, 138, 271-280 (1998).

* cited by examiner

*Primary Examiner*—Phyllis G. Spivack
(74) *Attorney, Agent, or Firm*—Frishauf, Holtz, Goodman & Chick, P.C.

(57) ABSTRACT

A blood lipid ameliorating composition containing atorvastatin in combination with an agent selected from the group consisting of a riboflavin derivative, a tocopherol compound, an ascorbic acid derivative, pantethine and taurine.

33 Claims, No Drawings

BLOOD LIPID AMELIORANT COMPOSITION

This is a Continuation-in-Part application of International Application No. PCT/JP01/10913 filed Dec. 12, 2001 which is incorporated herein by reference in its entirety.

BACKGROUND OF THE INVENTION

The present invention relates to blood lipid ameliorating compositions that contain atorvastatin in combination with one or more ingredients selected from the group consisting of a riboflavin derivative, a tocopherol derivative, an ascorbic acid derivative, pantethine and taurine.

Atorvastatin reduces total cholesterol levels in the blood by inhibiting HMG-CoA reductase activity.

It is known that each of a riboflavin derivative, a tocopherol derivative, an ascorbic acid derivative, pantethine and taurine alone reduces cholesterol levels in the blood.

Furthermore, it is known that a co-administration of a HMG-CoA reductase inhibitors with either a tocopherol derivative or an ascorbic acid derivative reduces total cholesterol levels in the blood in addition to counteracting decrease of tocopherol or ascorbic acid that were decreased in the organism (Japanese Patent Kohyo No. Hei 8-505853).

However, it remains unknown whether co-administration of atorvastatin with one of a riboflavin derivative, a tocopherol derivative, an ascorbic acid derivative, pantethine or taurine synergistically decreases total cholesterol levels in the blood.

Furthermore, although atorvastatin is a highly safe remedy, it is desirable that atorvastatin can reduce total cholesterol levels in the blood when administered at lower doses, because it is necessary to administer atorvastatin for a long period.

BRIEF DESCRIPTION OF THE INVENTION

The present inventors investigated drug compositions that decrease total cholesterol levels in the blood, and found that co-administration of atorvastatin with a certain vitamin or taurine reduces the total cholesterol levels in the blood at further lower doses, and completed the present invention.

The present invention comprises a serum lipid ameliorating composition comprising atorvastatin and one or more ingredients selected from the group consisting of a riboflavin derivative, a tocopherol derivative, an ascorbic acid derivative, pantethine and taurine. The present invention also comprises the use of this composition to ameliorate blood lipid levels.

DETAILED DESCRIPTION OF THE INVENTION

The term 'atorvastatin' includes [R-(R*,R*)]-2-(4-fluorophenyl)-β,δ-dihydroxy-5-(1-methylethyl)-3-phenyl-4-[phenylamino]carbonyl]-1H-pyrrole-1-heptanoic acid and its salt (particularly calcium salt).

The term 'riboflavin derivative' includes riboflavin and riboflavin esters such as riboflavin butyrate. Among these compounds riboflavin, riboflavin sodium phosphate, riboflavin butyrate, flavin-adenine dinucleotide, or flavin-adenine dinucleotide sodium salt are preferred. Riboflavin sodium phosphate and riboflavin butyrate are more preferred, and riboflavin butyrate is the most preferred compound.

The term 'tocopherol derivative' includes tocopherol (the racemate and its optical enantiomers) and esters of tocopherol such as tocopherol acetate (the racemate and its optical enantiomers). Among these substances d-α-tocopherol succinate, dl-α-tocopherol succinate, dl-α-tocopherol calcium succinate, d-α-tocopherol acetate, dl-tocopherol acetate, d-α-tocopherol or dl-α-tocopherol are preferred, dl-α-tocopherol succinate or d-α-tocopherol acetate are more preferred, and d-α-tocopherol acetate is the most preferred compound.

The term 'ascorbic acid derivative' includes ascorbic acid, ascorbates such as sodium ascorbate, and ascorbic acid esters such stearyl ascorbate. Among these compounds ascorbic acid, sodium ascorbate or calcium ascorbate are preferred and ascorbic acid is more preferred.

Pantethine is 2,4-dihydroxy-N-[3-[(2-mercaptoethyl)amino]-3-oxopropyl]-3,3-dimethylbutanamide.

The term 'taurine' includes 2-aminoethanesulfonic acid and salts thereof.

The term 'total cholesterol in the blood' includes the total levels of cholesterol and cholesterol esters in the blood.

The term 'ameliorating' in the expression 'blood lipid ameliorating composition' indicates that the levels are decreased by clinically significant amounts following administration of the composition.

The weight percent of atorvastatin contained in solid preparations of the blood lipid ameliorating composition of the present invention is 0.01 to 5%, preferably 0.05 to 3%.

The weight percent of riboflavin derivative in the solid preparations is typically 0.002 to 40%, preferably 0.01 to 20.0%. Furthermore, the weight percent of ascorbic acid derivative is typically 0.05 to 50.0%, preferably 0.5 to 25.0%. The weight percent of tocopherol derivative is typically 0.002 to 40.0%, preferably 0.02 to 20%, the weight percent of pantethine is typically 0.3 to 50%, preferably 1.0 to 20%, and that of taurine is typically 0.3 to 50%, preferably 1 to 25%.

The content of atorvastatin contained in liquid and solution preparations of the blood lipid ameliorating composition of the present invention is typically 0.05 to 2 mg/mL, and preferably 0.1 to 1 mg/mL; that of riboflavin derivative is typically 0.05 to 5 mg/mL, preferably 0.1 to 3 mg/mL. In addition, the content of ascorbic acid derivative is typically 1 to 20 mg/mL, preferably 2 to 10 mg/mL. The content of tocopherol derivative is typically 0.5 to 5 mg/mL, preferably 1.5 to 3 mg/mL. The content of pantethine is typically 0.5 to 20 mg/mL, preferably 1 to 10 mg/mL; and that of taurine is typically 1.0 to 50 mg/mL, preferably 2 to 35 mg/mL.

Practical preparations of the blood lipid ameliorating compositions are tablets, granules (involving powders), capsules, and liquids and solutions, etc., and are manufactured following addition of the required additive agents or materials, if desired, according to conventional methods described in The Pharmacopeia of Japan.

In the preparations described above, additive agents that are conventionally used can be employed based on the preparation.

For instance, in the case of tablets, lactose and crystalline cellulose are used as diluents, magnesium aluminometasilicate, etc., are used as stabilizing agents, hydroxypropylcellulose, etc., are used as binders, and magnesium stearate is used as a lubricant.

In granules and capsules, lactose and purified sucrose are used as diluents, magnesium aluminometasilicate is used as a stabilizing agent, cornstarch, etc., are used as adsorbents, and hydroxypropylcellulose and polysorbate, etc., are used as binders.

In liquids and solutions, D-sorbitol solution and honey, etc., are used as sweeteners, dl-malic acid, etc., are used as flavoring agents, disodium dihydrogen ethylenediamine tetraacetate, etc., are used as stabilizing agents, ethanol is used as a co-solvent, and polyoxyethylene hydrogenated castor oil stearate 60, etc., are used as a solubilizer.

In the preparations described above, a disintegrator such as crospovidone, etc.; an adsorbent such as calcium silicate, etc.; a coloring agent such as red ferric oxide and caramel, etc.; a pH modifier such as sodium benzoate, etc.; and a flavor may be used.

When the composition in the present invention is administered, each component of the composition can be administered at the same time or individually at certain intervals.

The term "administration at the same time" described above has no particular limitation, provided that each component of the composition is administered at roughly the same time. However, it is desirable that a single composition containing all components is administered.

The term "administration of individual components at certain intervals" described above has no particular limitation, provided that each component of the composition is individually administered at different times. In this case, one component is administered and the other components can then be administered within a certain defined time period.

In the case that 3 or more components in total are contained in the composition, the term "administration of these components at the same time or individually at different times" described above involves the following ways of administration: all components are administered at the same time; all components are administered individually at different times; 2 or more components are administered at the same time and the remaining component(s) are administered at different times; 2 or more components are administered at different times and the remaining components are administered at the same time; and so on.

EXAMPLES

The present invention is described in more detail by way of the following examples. However, the present invention is not limited to these examples.

Test Example 1

Tablets (1) Composition

TABLE 1

|  | RFV 4 tabs (800 mg) | AA 4 tabs (1200 mg) | Tocoph 4 tabs (900 mg) | Pant 4 tabs (1200 mg) | Taurine 4 tabs (1200 mg) |
| --- | --- | --- | --- | --- | --- |
| Atorvastatin | 20 mg | 20 mg | 20 mg | 20 mg | 20 mg |
| RFVb | 100 mg | — | — | — | — |
| Ascorbic acid | — | 500 mg | — | — | — |
| dl-α-Tocopherol succinate | — | — | 200 mg | — | — |
| Pantethine | — | — | — | 500 mg | — |
| Taurine (Aminoethanesulfonic acid) | — | — | — | — | 500 mg |
| Crystalline cellulose | 120 mg | 12 mg | 12 mg | 12 mg | 120 mg |
| Magnesium aluminometasilicate | 144 mg | — | — | — | 144 mg |
| Sucrose esters fatty acids | — | 140 mg | 108 mg | 140 mg | — |
| Hydroxypropylcellulose | 96 mg | 48 mg | 48 mg | 48 mg | 96 mg |
| Magnesium stearate | 24 mg | 24 mg | 24 mg | 24 mg | 24 mg |
| Crospovidone | 100 mg | 48 mg | 48 mg | 48 mg | 100 mg |
| Lactose | aq | aq | aq | aq | aq |

RFVb: Riboflavin butyrate,
RFV: Riboflavin,
AA: Ascorbic acid,
Tocoph: Tocopherol,
Pant: Pantethine,
tabs: tablets,
aq: appropriate quantity (2) Manufacturing Methods The amount of each component described above is weighed and prepared according to the methods described in the "General Rules for Preparation of Tablets" in The Pharmacopeia of Japan.

Test Example 2

Granules (1) Composition

TABLE 2

|  | RFV 4 packs (4 g) | AA 4 packs (5.2 g) | Tocoph 4 packs (4.2 g) | Pant 4 packs (4.6 g) | Taurine 4 packs (5.2 g) |
| --- | --- | --- | --- | --- | --- |
| Atorvastatin | 20 mg | 20 mg | 20 mg | 20 mg | 20 mg |
| RFVb | 100 mg | — | — | — | — |
| Ascorbic acid | — | 1.0 g | — | — | — |
| dl-α-Tocopherol succinate | — | — | 200 mg | — | — |
| Pantethine | — | — | — | 500 mg | — |
| Taurine (Aminoethanesulfonic acid) | — | — | — | — | 1.0 g |
| Purified sucrose | 1.4 g | 1.6 g | 1.4 g | 1.6 g | 1.4 g |
| Stevia extracts | — | 16 mg | — | 16 mg | — |
| Cornstarch | 1.2 g | 1.2 g | 1.2 g | 1.2 g | 1.2 g |
| Polysorbate 80 | 80 mg | 48 mg | 48 mg | 48 mg | 80 mg |
| Magnesium aluminometasilicate | 144 mg | — | 128 mg | — | 144 mg |
| Magnesium stearate | 24 mg | 24 mg | 24 mg | 24 mg | 24 mg |
| Lactose | aq | aq | aq | aq | aq |

RFVb: Riboflavin butyrate,
RFV: Riboflavin,
AA: Ascorbic acid,
Tocoph: Tocopherol,
Pant: Pantethine,
packs: packages,
aq: appropriate quantity (2) Manufacturing Methods The amount of each component described above is weighed and prepared according to the methods described in the "General Rules for Preparations of Granules" in The Pharmacopeia of Japan.

Test Example 3

Capsules

Components

TABLE 3

|  | RFV 4 caps | AA 4 caps | Tocoph 4 caps | Pant 4 caps | Taurine 4 caps |
| --- | --- | --- | --- | --- | --- |
| Atorvastatin | 20 mg | 20 mg | 20 mg | 20 mg | 20 mg |
| RFVb | 100 mg | — | — | — | — |
| AA | — | 500 mg | — | — | — |
| dl-α-Tocopherol succinate | — | — | 200 mg | — | — |
| Pantethine | — | — | — | 500 mg | — |
| Taurine (Aminoethanesulfonic acid) | — | — | — | — | 500 mg |
| Cornstarch | 960 mg | 960 mg | 840 mg | 960 mg | 960 mg |
| Polysorbate 80 | 80 mg | 48 mg | 48 mg | 48 mg | 80 mg |
| Magnesium aluminometasilicate | 144 mg | — | 128 mg | — | 144 mg |
| Magnesium stearate | 24 mg | 24 mg | 24 mg | 24 mg | 24 mg |
| Lactose | aq | aq | aq | aq | aq |
| Subtotal | 1520 mg | 1940 mg | 1580 mg | 1940 mg | 2008 mg |
| Capsule | 320 mg | 640 mg | 320 mg | 640 mg | 640 mg |
| Total | 1840 mg | 2580 mg | 1900 mg | 2580 mg | 2648 mg |

RFVb: Riboflavin butyrate,
RFV: Riboflavin,
AA: Ascorbic acid,
Tocoph: Tocopherol,
Pant: Pantethine,
caps: capsules,
aq: appropriate quantity (2) Manufacturing Methods The amount of each component described above is weighed and prepared according to the methods described in the "General Rules for Preparations of Granules" in The Pharmacopeia of Japan, and hard capsules are prepared by filling the granules into capsules.

Test Example 4

Liquids and Solutions (1) Components

TABLE 4

|  | RFV 100 mL | AA 100 mL | Tocoph 100 mL | Pant 100 mL | Taurine 100 mL |
| --- | --- | --- | --- | --- | --- |
| Atorvastatin | 20 mg | 20 mg | 20 mg | 20 mg | 20 mg |
| RFV sodium | 200 mg | — | — | — | — |
| Ascorbic acid | — | 500 mg | — | — | — |
| dl-α-Tocopherol acetate | — | — | 50 mg | — | — |
| Pantethine | — | — | — | 500 mg | — |
| Taurine (Aminoethanesulfonic acid) | — | — | — | — | 500 mg |
| D-Sorbitol solution | 4 g | 6 g | 4 g | 6 g | 4 g |
| Honey | 7 g | 8 g | 7 g | 8 g | 7 g |
| dl-Malic acid | 200 mg | — | 200 mg | — | 200 mg |
| DDEDTA | 20 mg | 20 mg | 20 mg | 20 mg | 20 mg |
| Ethanol | 2 mL | 2 mL | 2 mL | 2 mL | 2 mL |
| PEHCO | 100 mg | 100 mg | 100 mg | 100 mg | 100 mg |
| Sodium benzoate | 60 mg | 60 mg | 60 mg | 60 mg | 60 mg |
| Flavor | trace | trace | trace | trace | trace |
| Distilled water | aq | aq | aq | aq | aq |

RFV: Riboflavin,
AA: Ascorbic acid,
Tocoph: Tocopherol,
Pant: Pantethine,
D-Sorbitol solution: D-Sorbitol solution (70%),
DDEDTA: Disodium dihydrogen ethylenediamine tetraacetate,
PEHCO: Polyoxyethylene hydrogenated castor oil stearate 60,
aq: appropriate quantity (2) Manufacturing Methods The amount of each component described above is weighed and prepared according to the methods described in the "General Rules for Preparations of Liquids and Solutions" in The Pharmacopeia of Japan.

Assay of Blood Lipid Ameliorating Effects

Test Methods (1) Test Compounds

Atorvastatin was synthesized at Chemtech Labo. Inc., and riboflavin butyrate, d-α-tocopherol acetate, ascorbic acid, pantethine and taurine were purchased from Mitsubishi- Tokyo Pharmaceutical Inc., Eisai Co., Ltd., NIPPON ROCHE K.K., Nacalai Tesque, Inc. and Dai-ich Pharmaceutical Co., Ltd., respectively.

(2) Test Animals

Beagle dogs aged 5 months were purchased from Covance Research Products Inc. and used after 1 month of quarantine and acclimatisation breeding.

(3) Preparation Forms for Administration, Methods for Preparing the Formulation, and Method for Stocking the Formulation The required amounts of atorvastatin or each component of the combination drug calculated from the body weight of each dog were weighed and filled in a gelatin capsule (½ ounce) purchased from TORPAC Inc. Capsules filled with atorvastatin were stocked in a refrigerator and those filled with combination drugs stocked at room temperature until use.

The combination drugs were filled in identical gelatin capsules.

(4) Route of Administration and Administration Period

Atorvastatin or combination drug capsules were forcibly orally administered to each of the test animals once daily between 9:00 and 12:30. Animals were fasted for 2 or 3 hr prior to administration of the capsules.

The administration period was 11 successive days.

(5) Preparation of Test Samples and Procedures

Blood (10 mL) was collected from the superficial radial vein 2 or 1 weeks prior to administration and 4, 8, and 12 days after administration was started. Animals were fasted for approximately 18 hr prior to blood collection. Collected blood was placed in a test tube, left at room temperature for 0.5–1 hr, then centrifuged (3,000 rpm for 10 min). The obtained serum was used for assays of blood levels of total cholesterol, lipid peroxides and triglycerides according to CEH-COD-POD (Cholesterol ester hydrolase-Cholesteroloxidase-Peroxidase) methods, Yagi's methods and GK-GPO-POD (Glycerokinase-Glycerolphosphateoxidase-Peroxidase) methods respectively. (For assay method, see: Kanai's Manual of Clinical Laboratory Medicine; 31st Edition (September 1998), Kanehara & Co., Ltd.).

All these levels were determined using a fluorometer (Hitachi, Ltd., F3000), a full automatic analyzer (Monarch, Instrumentation Laboratory), and an automatic analyzer (7170, Hitachi, Ltd.).

Results

Total cholesterol levels and so forth in the blood collected from dogs treated with either atorvastatin alone or a combination drug consisting of atorvastatin plus one of riboflavin butyrate, d-α-tocopherol acetate, ascorbic acid, pantethine and taurine were determined. All these values were converted to their relative ratios against their averaged pre-dosing levels (100) determined 2 and 1 weeks prior to drug administration. The averaged value in each group was obtained from 5 animals per group.

(Effects of Co-administration of Atorvastatin and Riboflavin Butyrate)

TABLE 5

| Test Substance | Dose (mg/kg) | Blood Total Cholesterol Levels after administration | | |
|---|---|---|---|---|
| | | 4 days | 8 days | 12 days |
| Atorvastatin alone | 2 | 102.9 | 95.5 | 90.9 |
| RFVb alone | 200 | 99.5 | 99.0 | 97.2 |
| Atorvastatin + RFVb | 2 200 | 94.9 | 88.0 | 89.3 |

RFVb: riboflavin butyrate (Effects of Co-administration of Atorvastatin and d-α-Tocopherol Acetate)

TABLE 6

| Test Substance | Dose (mg/kg) | Blood Total Cholesterol Levels after administration | | |
|---|---|---|---|---|
| | | 4 days | 8 days | 12 days |
| Atorvastatin alone | 2 | 102.9 | 95.5 | 90.9 |
| Tocoph alone | 300 | 97.7 | 95.1 | 97.5 |
| Atorvastatin + Tocoph | 2 300 | 93.7 | 84.2 | 87.7 |

Tocoph: d-α-tocopherol acetate

TABLE 7

| Test Substance | Dose (mg/kg) | Blood Lipid Peroxide Levels after administration | | |
|---|---|---|---|---|
| | | 4 days | 8 days | 12 days |
| Atorvastatin alone | 2 | 104.5 | 84.4 | 80.9 |
| Tocoph alone | 300 | 106.3 | 119.0 | 75.9 |
| Atorvastatin + Tocoph | 2 300 | 79.5 | 68.3 | 68.1 |

Tocoph: d-α-tocopherol acetate (Effects of Co-administration of Atorvastatin and Ascorbic Acid)

TABLE 8

| Test Substance | Dose (mg/kg) | Blood FFA Levels after administration | | |
|---|---|---|---|---|
| | | 4 days | 8 days | 12 days |
| Atorvastatin alone | 2 | 102.9 | 95.5 | 90.9 |
| AA alone | 500 | 95.9 | 96.7 | 98.9 |
| Atorvastatin + AA | 2 500 | 96.3 | 87.6 | 87.9 |

AA: ascorbic acid (Effects of Co-administration of Atorvastatin and Pantethine)

TABLE 9

| Test Substance | Dose (mg/kg) | GOT Levels after administration | | |
|---|---|---|---|---|
| | | 4 days | 8 days | 12 days |
| Atorvastatin alone | 2 | 102.9 | 95.5 | 90.9 |

TABLE 9-continued

| Test Substance | Dose (mg/kg) | GOT Levels after administration | | |
|---|---|---|---|---|
| | | 4 days | 8 days | 12 days |
| Pantethine alone | 300 | 94.0 | 87.6 | 85.2 |
| Atorvastatin + Pantethine | 2 300 | 88.7 | 78.2 | 70.7 |

TABLE 10

| Test Substance | Dose (mg/kg) | Blood Lipid Peroxide Levels after administration | | |
|---|---|---|---|---|
| | | 4 days | 8 days | 12 days |
| Atorvastatin alone | 2 | 104.5 | 84.4 | 80.9 |
| Pantethine alone | 300 | 82.5 | 105.0 | 87.5 |
| Atorvastatin + Pantethine | 2 300 | 90.2 | 74.0 | 69.2 |

(Effects of Co-administration of Atorvastatin and Taurine)

TABLE 11

| Test Substance | Dose (mg/kg) | Blood Total Cholesterol Levels after administration | | |
|---|---|---|---|---|
| | | 4 days | 8 days | 12 days |
| Simvastatin alone | 2 | 102.9 | 95.5 | 90.9 |
| Taurine alone | 1000 | 95.9 | 90.2 | 87.2 |
| Atorvastatin + Taurine | 2 1000 | 87.5 | 75.2 | 73.7 |

TABLE 12

| Test Substance | Dose (mg/kg) | Blood Triglyceride Levels after administration | | |
|---|---|---|---|---|
| | | 4 days | 8 days | 12 days |
| Simvastatin alone | 2 | 87.1 | 86.7 | 74.1 |
| Taurine alone | 1000 | 98.6 | 95.8 | 80.8 |
| Atorvastatin + Taurine | 2 1000 | 83.5 | 77.7 | 65.4 |

The present invention, drug compositions of atorvastatin plus ascorbic acid and so forth, exerts excellent blood total cholesterol-lowering effects and is useful as a blood lipid ameliorating agent.

Although the dose of compounds used according to the invention may widely vary depending on the extent of diseases and age of patients, (e.g. human patients), the dose of one administration of atorvastatin is normally within the range of from 0.01 mg/kg to 20 mg/kg, preferably from 0.1 mg/kg to 2 mg/kg, administered once or several times a day dependent on the extent of diseases.

The dose of one administration of riboflavin derivative is normally within the range of from 0.004 mg/kg to 24 mg/kg, preferably from 0.04 mg/kg to 2.4 mg/kg, administered once or several times a day dependent on the extent of diseases.

The dose of one administration of tocopherol derivative is normally within the range of from 0.02 mg/kg to 60 mg/kg, preferably from 0.2 mg/kg to 6.0 mg/kg, administered once or several times a day dependent on the extent of diseases.

The dose of one administration of ascorbic acid derivative is normally within the range of from 0.1 mg/kg to 400 mg/kg, preferably from 1 mg/kg to 40 mg/kg, administered once or several times a day dependent on the extent of diseases.

The dose of one administration of pantethine is normally within the range of from 0.06 mg/kg to 120 mg/kg, preferably from 0.6 mg/kg to 12 mg/kg, administered once or several times a day dependent on the extent of diseases.

The dose of one administration of taurine is normally within the range of from 1 mg/kg to 600 mg/kg, preferably from 10 mg/kg to 60 mg/kg, administered once or several times a day dependent on the extent of diseases.

What is claimed is:

1. A method of ameliorating blood lipid levels, selected from the group consisting of total cholesterol levels, lipid peroxide levels, free fatty acid levels and triglyceride levels, said method comprising administering, in combination, to a warm-blooded animal in need thereof, in amounts to form a synergistically effective mixture for ameliorating said blood lipid levels, atorvastatin and agent selected from the group consisting of a riboflavin derivative, a tocopherol derivative, an ascorbic acid derivative, pantethine and taurine.

2. A method according to claim 1 wherein said atorvastatin and said agent selected from the group consisting of said riboflavin derivative, said tocopherol derivative, said ascorbic acid derivative, said pantethine and said taurine, are administered in the form of a combination pharmaceutical composition.

3. A method according to claim 1 wherein said atorvastatin and said agent selected from the group consisting of said riboflavin derivative, said tocopherol derivative, said ascorbic acid derivative, said pantethine and said taurine are administered separately and simultaneously.

4. A method according to claim 1 wherein said atorvastatin and said agent selected from the group consisting of said riboflavin derivative, said tocopherol derivative, said ascorbic acid derivative, said pantethine and said taurine, are administered separately and non-simultaneously.

5. A method according to claim 1 wherein the ingredient is said riboflavin derivative which is selected from the group consisting of riboflavin, flavin-adenine dinucleotide and flavin-adenine dinucleotide sodium salt.

6. A method according to claim 1 wherein the ingredient is said riboflavin derivative which is riboflavin sodium phosphate.

7. A method according to claim 1 wherein the ingredient is said riboflavin derivative which is riboflavin butyrate.

8. A method according to claim 1 wherein the ingredient is said tocopherol derivative which is selected from the group consisting of dl-α-tocopherol succinate, dl-α-tocopherol calcium succinate, dl-α-tocopherol acetate, d-α-tocopherol and dl-α-tocopherol.

9. A method according to claim 1 wherein the ingredient is said tocopherol derivative which is d-α-tocopherol succinate.

10. A method according to claim 1 wherein the ingredient is said tocopherol derivative which is d-α-tocopherol acetate.

11. A method according to claim 1 wherein the ingredient is said ascorbic acid derivative which is selected from the group consisting of sodium ascorbate and calcium ascorbate.

12. A method according to claim 1 wherein the ingredient is said ascorbic acid derivative which is ascorbic acid.

13. A method of ameliorating blood lipid levels according to claim 1, said method comprising administering, in combination, to a warm-blooded animal in need thereof, in amounts to form a synergistically effective mixture for ameliorating said blood lipid levels, atorvastatin and riboflavin succinate.

14. A method according to claim 13 wherein said atorvastatin and said riboflavin succinate are administered in the form of a combination pharmaceutical composition.

15. A method according to claim 13 wherein said atorvastatin and said riboflavin succinate are administered separately and simultaneously.

16. A method according to claim 13 wherein said atorvastatin and said riboflavin succinate are administered separately and non-simultaneously.

17. A method of ameliorating blood lipid levels according to claim 1, said method comprising administering, in combination, to a warm-blooded animal in need thereof, in amounts to form a synergistically effective mixture for ameliorating said blood lipid levels, atorvastatin and ascorbic acid.

18. A method according to claim 17 wherein said atorvastatin and said ascorbic acid are administered in the form of a combination pharmaceutical composition.

19. A method according to claim 17 wherein said atorvastatin and said ascorbic acid are administered separately and simultaneously.

20. A method according to claim 17 wherein said atorvastatin and said ascorbic acid are administered separately and non-simultaneously.

21. A method of ameliorating blood lipid levels according to claim 1, said method comprising administering, in combination, to a warm-blooded animal in need thereof, in amounts to form a synergistically effective mixture for ameliorating said blood lipid levels, atorvastatin and d-α-tocopherol acetate.

22. A method according to claim 21 wherein said atorvastatin and said d-α-tocopherol acetate are administered in the form of a combination pharmaceutical composition.

23. A method according to claim 21 wherein said atorvastatin and said d-α-tocopherol acetate are administered separately and simultaneously.

24. A method according to claim 21 wherein said atorvastatin and said d-α-tocopherol acetate are administered separately and non-simultaneously.

25. A method of ameliorating blood lipid levels according to claim 1, said method comprising administering, in combination, to a warm-blooded animal in need thereof, in amounts to form a synergistically effective mixture for ameliorating said blood lipid levels, atorvastatin and pantethine.

26. A method according to claim 25 wherein said atorvastatin and said pantethine are administered in the form of a combination pharmaceutical composition.

27. A method according to claim 25 wherein said atorvastatin and said pantethine are administered separately and simultaneously.

28. A method according to claim 25 wherein said atorvastatin and said pantethine are administered separately and non-simultaneously.

29. A method of ameliorating blood lipid levels according to claim 1, said method comprising administering, in combination, to a warm-blooded animal in need thereof, in amounts to form a synergistically effective mixture for ameliorating said blood lipid levels, atorvastatin and taurine.

30. A method according to claim 29 wherein said atorvastatin and said taurine are administered in the form of a combination pharmaceutical composition.

31. A method according to claim 29 wherein said atorvastatin and said taurine are administered separately and simultaneously.

32. A method according to claim 29 wherein said atorvastatin and said taurine are administered separately and non-simultaneously.

33. A method according to claim 1 wherein the warm-blooded animal is a human.

\* \* \* \* \*